(12) United States Patent
Fanta et al.

(10) Patent No.: US 6,350,545 B2
(45) Date of Patent: *Feb. 26, 2002

(54) SULFONYLIMIDE COMPOUNDS

(75) Inventors: Alan David Fanta, Minneapolis; Phat tan Pham, Little Canada; Steven Joseph Hamrock, St. Paul, all of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/139,374

(22) Filed: Aug. 25, 1998

(51) Int. Cl.[7] ............... H01M 10/40; C07C 313/00; C07C 315/00

(52) U.S. Cl. ............ 429/307; 429/314; 429/316; 429/317; 540/468; 549/11; 564/102; 568/30; 568/36

(58) Field of Search ............... 540/467, 468, 540/490; 549/11; 564/102, 511; 568/30, 36; 429/307, 314, 316, 317, 324, 347

(56) References Cited

U.S. PATENT DOCUMENTS

| | | | |
|---|---|---|---|
| 3,793,079 A | * | 2/1974 | Brown et al. |
| 4,818,644 A | | 4/1989 | Armand |
| 5,273,840 A | * | 12/1993 | Dominey |
| 5,350,646 A | | 9/1994 | Armand et al. |
| 5,514,493 A | * | 5/1996 | Waddell et al. ............ 429/199 |
| 5,534,370 A | | 7/1996 | Kita et al. |
| 5,538,812 A | * | 7/1996 | Lee et al. ............ 508/30 X |
| 5,573,872 A | * | 11/1996 | Shackle ............ 429/307 |
| 5,654,112 A | * | 8/1997 | Itou et al. |
| 5,691,081 A | * | 11/1997 | Krause et al. |
| 5,837,400 A | * | 11/1998 | Baudry et al. ............ 429/307 |
| 6,013,393 A | * | 1/2000 | Taniuchi et al. ......... 429/317 X |
| 6,063,522 A | * | 5/2000 | Hamrock et al. ....... 429/324 X |

FOREIGN PATENT DOCUMENTS

| | | |
|---|---|---|
| EP | 0 850 921 A1 | 1/1998 |
| EP | 850 920 | 7/1998 |
| JP | 8-217745 | 8/1996 |
| WO | WO 95/26056 | 9/1995 |

OTHER PUBLICATIONS

D. Argyropoulos et al., "Condensation Products from Imidobis(sulfuryl Chloride)", Journal of Applied Polymer Science, vol. 26; 3073–3084 (1981), (Month unknown).

Fusaji Kita et all, "On the Characteristics of Electrolytes with New Lithium Imide Salts", 62nd Electrochemical Society Congress volume, p. 256 (1995), (Month unknown).

Schneider et al., "Imidodisulfamide derivatives," Chemical Abstracts, vol. 68, No. 3, p. 1167, XP002102195, (Jan. 1968).

Kita et al., "On the Characteristics of Electrolytes with New Lithium Imide Salts," Journal of Power Sources, vol. 68, No. 2, pp. 307–310, (1997), (Month unknown).

* cited by examiner

*Primary Examiner*—Stephen Kalafut
(74) *Attorney, Agent, or Firm*—Robert H. Jordan

(57) ABSTRACT

Novel sulfonylinide and sulfonylmethide compounds are described which are useful as conductive salts. Also described is the use of the above compounds in salt form in battery electrolytes, particular salts having mixed perfluorocaron and hydrocarbon groups or having all hydrocarbon groups. The above salts are less expensive to produce and still exhibit excellent conductivity and low corrosivity.

20 Claims, No Drawings

SULFONYLIMIDE COMPOUNDS

FIELD OF THE INVENTION

This invention relates to sulfonylimide conductive salts having mixed fluorocarbon and hydrocarbon groups or having all hydrocarbon groups, and the use thereof in electrolytes for electrochemical cells, such as lithium batteries.

BACKGROUND

Industry is continually searching for novel compounds which can provide ionic conductivity when dissolved or dispersed in other materials. These compounds often find use, for example, as conductivity additives or enhancers, as cationic polymerization initiators or catalysts, as anti-static additives, as electrochemical sensors, and as surfactants. Such compounds are especially useful when employed in combination with other materials to form electrolytes to conduct electrical charge, for example, when used in electrochemical cells and devices such as batteries, fuel cells, electrochromic devices, capacitors, and supercapacitors.

With respect to the specific application of electrolyte compounds in electrochemical cells and devices, there is both a current and projected future demand for high energy density, lightweight, rechargeable power sources for use in automotive, industrial and consumer markets. Many of these needs can be met by lithium-ion battery technology, which requires the use of electrolytic salts dissolved in a non-aqueous solvent or polymer to act as an electrolyte. This electrolyte solution acts as the medium through which ionic conduction can occur between electrodes, providing charge balance within an electrochemical cell such as a battery.

Of course, new electrolytic compounds must exhibit specific chemical and physical properties to be useful in electrochemical cells and devices. Of primary importance, the compounds must exhibit good ionic conductivity and should be thermally and electrochemically stable. Additionally, the compounds must also exhibit good solubility at high concentration in common electrolyte solvents and/or polymers; they should exhibit inertness to other battery components (e.g., not cause corrosion of electrodes or current collectors); they should be relatively non-toxic; they should have acceptable environmental impact, and preferably they should be able to be produced at an economically feasible price. In the case of secondary (i.e., rechargeable) batteries, the compounds should exhibit good cycling behavior at room temperature and elevated temperature and should produce electrochemical cells that can be operated and maintained with minimal concerns for safety (e.g., explosions caused by thermal runaway).

There are currently only a small number electrolytic compounds known to be suitable for use in lithium-ion batteries; all are lithium salts and all have identifiable drawbacks. The most common electrolyte compound is $LiPF_6$, which exhibits good conductivity and corrosion resistance, but is thermally and hydrolytically unstable, decomposing to liberate fluoride ion which is detrimental to cell performance. Other compounds having potential uses in lithium electrolytes include $LiAsF_6$ (toxic), $LiBF_4$ (relatively poor conductivity, thermally and hydrolytically unstable), and $LiClO_4$ (thermally unstable, potentially explosive). There are also a number of known organofluorine lithium compounds, but each of these has its own individual shortcomings. Molecules like $LiOSO_2CF_3$ and $LiN(SO_2CF_3)_2$ are thermally very stable but can be corrosive to aluminum current collectors at the operative voltage of a lithium ion cell, and $LiC(SO_2CF_3)_3$ is very expensive to prepare.

There is a continuing need for new electrolyte compounds which can perform at useful conductivity levels, and that are easily handled and produced at a reasonable cost.

SUMMARY OF THE INVENTION

Conductive ionic compounds have been discovered that are lower cost alternatives to the relatively expensive perfluorinated sulfonates, sulfonylimides and sulfonylmethides now commercially used in electrochemical cells such as lithium batteries, fuel cells, capacitors, supercapacitors and electrochromic windows. These ionic compounds are analogous to perfluoroalkanesulfonylimide compounds in which some or all of the perfluoroalkyl groups have been replaced with oxygen or nitrogen heteroatoms attached to fluorine-free organic groups. By having part or even all of the expensive perfluoroalkyl groups replaced, the compounds of this invention can be made at a lower cost per pound and, having lower molecular weights, can be used at lower weight concentrations in electrolytes to produce a given molarity solution. Nonetheless, these relatively inexpensive compounds exhibit good conductivity and low corrosivity.

The present invention includes sulfonylimide compounds which are particularly useful as conductive salts in battery electrolytes.

In one aspect, the present invention includes novel salts of the Formula I:

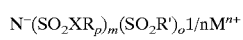

wherein:
  m is 1 or 2 and m+o is 2;
  X is independently O or N;
  p is 1 when X is O, and p is 2 when X is N;
  R is each independently a monovalent hydrocarbon group; two R groups when taken together form a divalent hydrocarbon group, e.g. an alkylene group or a 1,2-phenylene group, joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;
  R' is a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a heteroatom; and
  $M^{n+}$ is a cation having a valence of n;
  with the proviso that when m is 2, $M^{n+}$ is a metal or alkylammonium cation of the formula $R''_4N^+$, where R" is independently alkyl having 1 to 4 carbon atoms.

A second aspect of the present invention includes an electrolyte for use in electrochemical cells containing:
  (a) a salt of the Formula I,

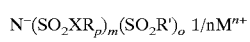

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group, e.g. an alkylene group or a 1,2-phenylene group, joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a heteroatom; and $M^{n+}$ is a cation having a valence of n; and (b) a matrix material.

A third aspect of the present invention includes a battery having at least one cathode, at least one anode and an electrolyte as defined above.

DETAILED DESCRIPTION OF THE INVENTION

Throughout this application the following definitions apply:

"Battery" includes all electrical energy storage devices, including capacitors, electrochromic devices, and electrochemical cells.

"Macromolecular material" refers to a homopolymer, copolymer, or combination thereof, which may or may not be cross-linked and/or plasticized.

"Gel" refers to a macromolecular material swollen with a liquid.

"Matrix" or "matrix material" refers to a medium (e.g., a solid, liquid, gel or plasticized polymer) in which salts according to Formula I may be dissolved or dispersed to form an jonically conductive electrolyte.

Voltages specified refer to electrical potential differences between a positive electrode measured relative to a Li/Li$^+$ reference electrode, except where otherwise noted.

The term "R" appearing in the Formula and throughout the specification can be a hydrocarbon group as defined below or a fluorocarbon group containing at least one carbon atom in a skeletal chain, such chain may be monovalent or divalent, branched or cyclic. The skeletal chain of carbon atoms can be interrupted by heteromoieties, such as divalent oxygen or trivalent nitrogen atoms each of which is bonded only to carbon atoms, or hexavalent sulfur atoms, each of which may be bonded to carbon, fluorine, or oxygen atoms, but preferably where such heteromoieties are present, such skeletal chain does not contain more than one said heteromoiety for every two carbon atoms.

A fluorocarbon group may be either a partially or fully fluorinated (i.e., perfluorinated) hydrocarbon chain. A partially fluorinated hydrocarbon chain exists where only a portion of the hydrogen atoms in the hydrocarbon has been replaced by fluorine atoms. In a fully fluorinated or perfluorinated hydrocarbon chain, essentially all of the hydrogen atoms, e.g. at least 90%, attached to carbon have been replaced by fluorine. Thus, the non-skeletal valence bonds are preferably carbon-to-fluorine bonds. However, an occasional carbon bonded hydrogen atom, bromine atom or chlorine atom may be present in a fully fluorinated hydrocarbon chain.

The total number of carbon atoms in a fluorocarbon group can vary and be, for example, 1 to 12, preferably 1 to 8, more preferably 1 to 4. Where the group is or contains a cyclic structure, such structure preferably has 5 or 6 ring members, one or two of which can be said heteromoieties, e.g., oxygen and/or nitrogen.

A "hydrocarbon group" refers to a monovalent or divalent straight or branched aliphatic group, a cycloaliphatic group, a cycloaliphatic-aliphatic group, or an aryl, biaryl or aralkyl group. These groups are further defined below.

"A straight or branched aliphatic group" refers to a hydrocarbon radical which is either in the form of a straight or branched chain and, in this case, ranging from 1 to 18 carbon atoms or as otherwise designated. A preferred embodiment includes alkyl straight or branched chain from 1 to 8 carbon atoms.

"Cycloaliphatic group" is a cyclic group having from 3 to 12 carbon atoms and refers to a cyclic saturated group. Thus, the group includes, for example, cyclopropyl, cyclobutyl, cyclopentyl, cyclohexyl, and the like.

The term "aryl" refers to a substituted or unsubstituted aromatic or heteroaromatic hydrocarbon such as, for example, phenyl, naphthyl, thienyl, pyridyl, pyrrolyl, and furyl. Preferred is a phenyl or naphthyl group that is unsubstituted or substituted by well recognized aromatic substituents such as, for example, alkyl of 1–4 carbon atoms, nitro, halo, trifluoromethyl or cyano. The phenyl or naphthyl group may be substituted by another phenyl or naphthyl group and then form a biaryl group, e.g. a biphenyl group. The phenyl or naphthyl group may further be substituted by a "reactive group" defined below. Particularly preferred aromatic groups include $C_6H_5$—, $C_{10}H_7$—, $CH_3C_6H_4$—, $O_2NC_6H_4$—, $FC_6H_4$—, $(CF_3)_2C_6H_3$—, and $NCC_6H_1$—. Particularly preferred divalent aromatic groups formed by two R groups include

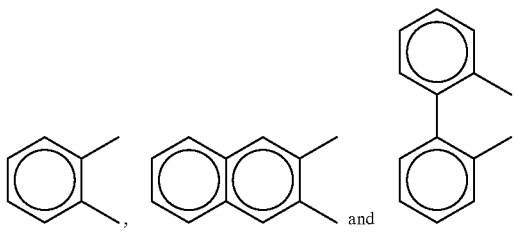

The term "reactive group" includes any group capable of reacting with itself or with other groups. For example, R and R' can contain a polymerizable group such as an olefinically unsaturated group (e.g., acrylate or allyl), an epoxide group, an isocyanato group and the like that would allow the sulfonylimide or sulfonylmethide to react with other reactive compounds, including other molecules of the same salt or molecules of a different reactive or polymerizable compound, via grafting or polymerization (cationic, anionic or free radical mechanism) to form a homopolymer or a copolymer. Such a homopolymer or copolymer material would be useful in electrolytes, particularly as single ion conductors. Suitable reactive groups may be chosen from those groups containing olefinic unsaturated groups (e.g., vinyl, allyl, vinylbenzyl, acryloyl or methacryloyl groups) or from those groups containing reactive heterocyclic ring structures (e.g., oxirane (epoxy), oxetane, azetidine or aziridine groups). The invention includes the homo- and copolymeric materials formed by the polymerization reaction involving compounds of Formula I where R and R' contain at least one polymerizable group.

A suitable reactive group may also be a hydroxy, amino, carboxyl, isocyanato, dialkoxyalkylsilyl, or trialkoxysilyl group. When the reactive group could interfere with reactions for preparing the desired imide or methide, the reactive group can be protected by reactants that are reversibly bound to it. For example, a double bond may be protected as a dihalo derivative and subsequently dehalogenated.

"Alkylene" refers to either straight or branched chain divalent organic groups which may join at both ends to other groups or atoms to form a ring. Preferred alkylene groups are ethylene and propylene.

"Fluoroalkylene" refers to either straight or branched chain divalent partially or fully fluorinated organic groups which may join at both ends to other groups or atoms to form a ring. Preferred fluoroalkylene groups are perfluoroethylene, perfluoropropylene and perfluorobutylene.

Suitable cations, $M^{m+}$, include alkali metal cations (e.g., $Li^+$, $Na^+$, $K^+$ and $Cs^+$), alkaline earth metal cations (e.g., $Mg^{2+}$, $Ca^{2+}$, $Sr^{2+}$ and $Ba^{2+}$), Group IIIA cations (e.g., $Al^{3+}$), transition metal cations (e.g., $Fe^{3+}$, $Fe^{2+}$, $Zn^{2+}$, $Ti^{4+}$ and $Cu^{2+}$), rare earth metal cations (e.g., $Ce^{4+}$ and $La^{3+}$), ammonium cations (i.e., $R_4N^+$, where R is independently alkyl, preferably having from 1 to 4 carbon atoms, aryl or hydrogen), sulfonium cations (i.e., $R_3S^+$), iodonium cations (i.e., $R_2I^+$), phosphonium cations (i.e., $R_4P^+$) and protons (i.e., $H^+$). Suitable cations also include organometallic cations such as ferrocenium cation, cyclopentadienyl (arene) $M^{m+}$, (arene) $M(CO)_3^{m+}$, $(arene)_2 M^{m+}$ and (cyclopentadienyl)$_2$ $M(CH_3)^{m+}$, wherein M is a transition metal. Preferably, for many battery applications, the cation is an alkali metal cation; most preferably, the cation is a lithium cation.

Suitable monovalent R and R' hydrocarbon groups include $CH_3$—, $C_2H_5$—, $(CH_3)_2CH$—, $(CH_3)_3CCH_2$—, $C_8H_{17}$—, $C_6H_5$—, $C_{10}H_7$—, $H_3CC_6H_4$—, $O_2NC_6H_4$—, $FC_6H_4$—, $NCC_6H_4$—, $(CF_3)_2C_6H_3$—, $CH_2=CH_2$—, $CH_2=CHCH_2$—, $CH_2=C(CH_3)$—, $CH_2=CHC(O)OC_2H_4$—, $CH_2=C(CH_3)C(O)OC_2H_4$—, $CH_2=CH-C_6H_4$—, $HC\equiv CCH_2$—, $OCN(CH_2)_6NH$—, $OCN-C_6H_4$—, $HOC_2H_4$—, $HOCH_2CH(OH)CH_2$—, $H_2NC_2H_4$—, $(CH_3O)_3SiC_3H_6$—, $(CH_3O)_2(CH_3)SiC_3H_6$—,

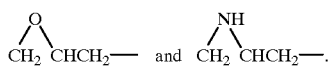

Suitable divalent groups formed when two R groups, two R' groups, or an R and R' group are taken together include —$CH_2CH_2$—, —$CH_2CH(—CH_3)$—,

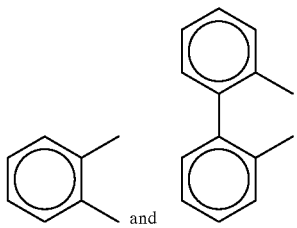

Suitable monovalent fluorocarbon groups include $CF_3$—, $C_2F_5$—, $C_4F_9$—, $C_8F_{17}$—, $(CF_3)_2NC_2F_4$—, $CF_3OC_2F_4$—.

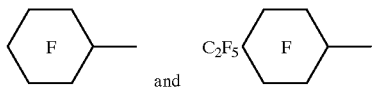

Suitable divalent fluorocarbon groups formed when two R' groups are taken together include —$CF_2CF_2$—, and —$CF_2CF(CF_3)$—.

Examples of particularly suitable sulfonylimide anions include the following:

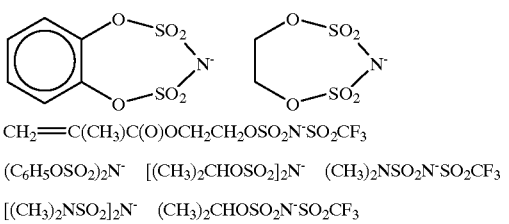

$CH_2=C(CH_3)C(O)OCH_2CH_2OSO_2N^-SO_2CF_3$ $(C_6H_5OSO_2)_2N^-$   $[(CH_3)_2CHOSO_2]_2N^-$   $(CH_3)_2NSO_2N^-SO_2CF_3$ $[(CH_3)_2NSO_2]_2N^-$   $(CH_3)_2CHOSO_2N^-SO_2CF_3$

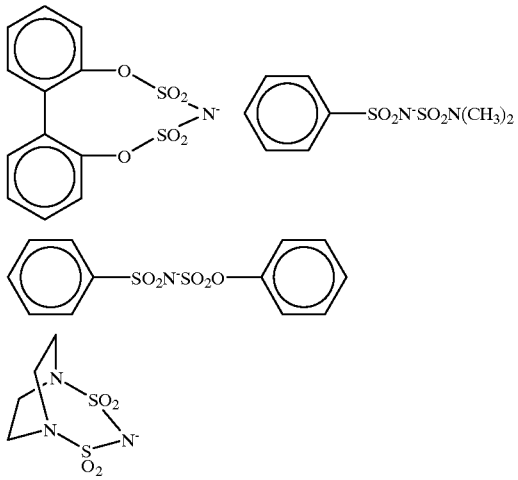

In general, the sulfonylimide compounds of this invention can be prepared by reacting the appropriate hydroxylic organic precursor (e.g., alcohol or phenol) or aminic organic precursor (e.g., amine or aniline) with a sulfonyl halide. The reaction is typically run in an aprotic solvent (e.g., acetonitrile) with a molar excess of tertiary amine (e.g., triethylamine) to consume the hydrogen halide acid generated and thus drive the reaction to completion. The reaction should be run at a temperature of approximately 0° C. to 25° C. to keep the exotherm under control. The resulting triethylammonium salt solution can be filtered to remove any solid by-products, and the filtrate can be stripped of solvent. To exchange the triethylammonium cation with the desired cation, neutralization can be conducted with an aqueous solution or dispersion of the base of the desired cation (e.g., its hydroxide, oxide or carbonate), water is removed, and the resulting solids washed with a water-immiscible solvent (e.g., diethyl ether). Further purification is possible by re-dissolving the solids in tetrahydrofuran and passing this solution through a short column of alumina.

Sulfonylimides having oxygen or nitrogen heteroatoms adjacent to the imide group may be conveniently prepared by reacting imidobis(sulfuryl chloride) (IBSC, $HN(SO_2Cl)_2$) with either a hydroxylic or aminic organic precursor as described by Argyropoulos et al. in *Journal of Applied Chemistry*, 26, 3073–3084 (1981), using the reaction conditions described above.

Procedures for making perfluoroalkanesulfonyl-substituted imide compounds are described in U.S. Pat. No. 5,652,072, which is herein incorporated by reference.

For some battery electrolyte compositions, it is desirable to add other conductive salts in order to maximize battery performance. Typically any conventional conductive salt known for chemical power sources may be used. For example, an additional conductive compound may include:

a cation selected from the group consisting of an alkali metal; an alkaline earth metal; a Group IIB metal; a Group IIIB metal; a transition metal; a rare earth metal; an ammonium cation such as tetraalkylammonium and trialkylammonium; and a proton; and an anion selected from the group consisting of $NO_3^-$, $Br^-$, $I^-$, $BF_4^-$, $PF_6^-$, $AsF_6^-$, $ClO_4^-$, $SbF_6^-$ and a perfluorinated anion, wherein the perfluorinated anion may be:

a perfluorinated sulfonate anion of the formula $R_{f0}SO_3^-$, in which $R_{f0}$ is a perfluoroalkyl group having between 1 and 12 carbon atoms which may contain straight, branched or cyclic moieties;

a perfluorinated acyclic imide anion of the formula $(R_{f1}SO_2)(R_{f2}SO_2)N^-$, in which $R_{f1}$ and $R_{f2}$ are each independently a perfluoroalkyl group of 1 to 8 carbon atoms which may contain straight, branched or cyclic moieties, with $R_{f1}$ and $R_{f2}$ having a total of up to 12 carbon atoms;

a perfluorinated cyclic imide anion of the formula

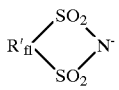

in which $R'_{f1}$ is a perfluoroalkylene moiety of 2 to 4 carbon atoms, optionally substituted by a straight or branched perfluoroalkyl group of 1 to 2 carbon atoms, with $R'_{f1}$ having a total of up to 6 carbon atoms;

a perfluorinated sulfonate, imide or methide anion of the formula $(R_{f3})(R_{f4})N(CF_2)_{n'}SO_2X^-$ or

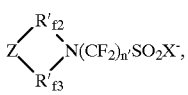

in which $R_{f3}$ and $R_{f4}$ independently are $-C_mF_{2m+1}$, or $-(CF_2)_qSO_2X^-$, and $R'_{f2}$ and $R'_{f3}$ independently are perfluoroalkylene moieties having the formula $-C_rF_{2r}-$; wherein $X^-$ is $-O^-$, $-N^-SO_2(R_{f5})$ or

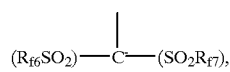

wherein $R_{f5}$, $R_{f6}$ and $R_{f7}$ independently are $-C_mF_{2m+1}$, $-(CF_2)_4-SO_2-X^-$,

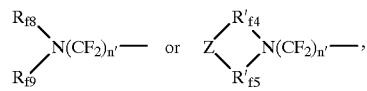

wherein $R_{f8}$ and $R_{f9}$ are each independently a straight, branched or cyclic perfluoroalkyl group of 1 to 8 carbon atoms, with $R_{f8}$ and $R_{f9}$ having a total of up to 12 carbon atoms;

Z is $-CF_2-$, $-O-$, $-N(R_{f10})-$ or $-SF_4-$, wherein $R_{f10}$ is $-C_mF_{2m+1}$, or $-(CF_2)_q-SO_2-X^-$;

$R'_{f4}$ and $R'_{f5}$ independently are perfluoroalkylene moieties having the formula $-C_rF_{2r}-$;

n' is 1 to 4 inclusive; m is 1 to 12 inclusive, preferably 1 to 8 inclusive; r is 1 to 4 inclusive; and q is 1 to 4 inclusive;

a bis(perfluoroalkylsulfonyl) methide anion of the formula $(R_{f11}SO_2)C^-(R)(SO_2R_{f12})$, in which $R_{f11}$ and $R_{f12}$ independently are perfluoroalkyl groups having between 1 and 12 carbon atoms, preferably between 1 and 4 carbon atoms, and R is H, Br, Cl, I, an alkyl group having between 1 and 20 carbon atoms, an aryl group or an alkaryl group;

and a tris(perfluoroalkylsulfonyl) methide anion of the formula $^-C(SO_2R_{f13})(SO_2R_{f14})(SO_2R_{f15})$, in which $R_{f13}$, $R_{f14}$, and $R_{f15}$ independently are perfluoroalkyl groups having between 1 and 12 carbon atoms, preferably between 1 and 4 carbon atoms.

Preferred additional conductive salts includes those having a lithium cation and having an anion selected from the group consisting of $PF_6^-$ anion; $ClO_4^-$ anion; $BF_4^-$ anion; a perfluorinated sulfonate anion of the formula $R_{f0}SO_3^-$, in which $R_{f0}$ is a perfluoroalkyl group having from 1 to 8 carbon atoms; a perfluorinated acyclic imide anion of the formula $(R_{f1}SO_2)(R_{f2}SO_2)N^-$, wherein $R_{f1}$ and $R_{f2}$ are each independently a straight or branched perfluoroalkyl group having from 1 to 8 carbon atoms, with $R_{f1}$ and $R_{f2}$ having a total of up to 10 carbon atoms; a perfluorinated cyclic imide anion of the formula:

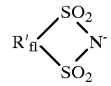

in which $R'_{f1}$ is a perfluoroalkylene moiety of 2 to 4 carbon atoms, optionally substituted by a straight or branched perfluoroalkyl group of 1 to 2 carbon atoms, with $R'_{f1}$ having a total of up to 6 carbon atoms; and a tris (perfluoroalkylsulfonyl)methide anion of the formula $^-C(SO_2R_{f13})(SO_2R_{f14})(SO_2R_{f15})$, in which $R_{f13}$, $R_{f14}$, and $R_{f15}$ independently are perfluoroalkyl groups having between 1 and 4 carbon atoms.

Most preferred additional conductive salts include $LiBF_4$, $LiAsF_6$, $LiClO_4$, $LiPF_6$, $LiNO_3$, $C_4F_9SO_3Li$, $C_8F_{17}SO_3Li$, $(CF_3SO_2)_2NLi$, $(C_2F_5SO_2)_2NLi$, $(C_8F_{17}SO_2)(CF_3SO_2)NLi$, $(C_8F_{17}SO_2)(C_2F_5SO_2)NLi$, $(CF_3SO_2)_2NNa$, $[(CF_3SO_2)_2N]_3Al$, $(CF_3)_2NC_2F_4SO_3Li$, $(CF_3SO_2)_3CLi$, $C_6H_5SO_2NLiSO_2CF_3$, $((CF_3)_2NC_2F_4SO_2)_2NLi$ and mixtures thereof.

To form the electrolyte composition, the conductive compounds are mixed with the matrix material such that the salts are at least partially dissolved or dispersed in the matrix material. The salts are preferably employed at a concentration such that the conductivity of the electrolyte solution is at or near its maximum value, although a wide range of other concentrations will also serve.

The matrix material may be in the form of a solid, liquid, gel or a liquid impregnated porous membrane. For battery applications, the matrix material is chosen to provide the particular conductance, viscosity, mechanical strength, reactivity and stability desired for the electrolyte.

Suitable matrix materials for preparing electrolyte solutions can be liquid, polymeric or mixtures of polymer and liquid. Examples of suitable solid matrix materials include polymers and copolymers such as polyethers like poly(ethylene oxide), polyesters, polyacrylates, polyphosphazenes, polysiloxanes, poly(propylene oxide), fluoropolymers (e.g., poly(vinylidene fluoride)), and poly(acrylonitrile), as well as the polymers and copolymers described in Armand et al., U.S. Pat. No. 4,505,997, incorporated herein by reference, and mixtures thereof. The polymers may be used in cross-linked or uncross-linked form and plasticized. Such materials are generally anhydrous, i.e., have a water content less than about 100 ppm, preferably less than about 50 ppm.

In batteries comprising a highly reducing electrode (such as lithium metal) and a liquid matrix material, the liquid is preferably a nonaqueous, polar, aprotic, organic solvent. Such liquids are generally anhydrous, i.e., have a water content less than about 100 ppm, preferably less than about 50 ppm. Examples of suitable aprotic liquids include linear ethers such as diethyl ether, diethylene glycol dimethyl ether, and 1,2-dimethoxyethane; cyclic ethers such as tetrahydrofuran, 2-methyltetrahydrofuran, dioxane, dioxolane, and 4-methyldioxolane; esters such as methyl formate, ethyl formate, methyl acetate, dimethyl carbonate, diethyl carbonate, propylene carbonate, ethylene carbonate, and butyrolactones (e.g. gamma butyrolactone); nitriles such as acetonitrile and benzonitrile; nitro compounds such as nitromethane or nitrobenzene; amides such as N,N-dimethylformamide, N,N-diethylformamide, and N-methylpyrrolidinone; sulfoxides such as dimethyl sulfoxide; sulfones such as dimethylsulfone; tetramethylene sulfone, and other sulfolanes; oxazolidinones such as N-methyl-2-oxazolidinone and mixtures thereof. Maximum conductivities of the electrolyte salts of this invention in typical nonaqueous, polar, aprotic liquid media (e.g., propylene carbonate) are generally in the range of 0.1–20 mS (milliSiemens) at room temperature, preferably greater than 1 mS.

Mixtures of matrix materials can be employed and are sometimes preferred in tailoring the matrix material's properties to provide optimum performance. In general, the amount of matrix material is selected such that the total salt concentration ranges from about 0.1M (moles per liter) to about 2.0M, preferably about 1M.

A preferred chemical power source of the present invention relates to a battery that includes at least one cathode, at least one anode, a separator and liquid electrolyte comprising conductive compounds and aprotic solvents.

The electrodes (i.e., anode and cathode) of, for example, a lithium battery generally consist of a metallic foil and particles of active material blended with a conductive diluent such as carbon black or graphite bound into a plastic material binder. Typical binders include polytetrafluoroethylene, polyvinylidene fluoride, ethylene-propylene-diene (EPDM) terpolymer, and emulsified styrene-butadiene rubber (SBR), and the binder may be cross-linked. The binder may also be, for example, a solid carbon matrix formed from the thermal decomposition of an organic compound. The metallic foil or composite electrode material is generally applied to an expanded metal screen or metal foil (preferably aluminum, copper or nickel) current collector using a variety of processes such as coating, casting, pressing or extrusion.

Examples of suitable battery anodes include lithium metal, lithium metal alloys, sodium metal, carbon-based materials such as graphite, coke, carbon fiber, pitch, transition metal oxides (such as $LiTi_5O_{12}$ and $LiWO_2$), and lithiated tin oxide. In the case of lithium ion batteries, the lithium may be intercalated into a host material such as carbon (i.e., to give lithiated carbon) or carbon alloyed with other elements (such as silicon, boron and nitrogen), a conductive polymer, or an inorganic host that is intercalatable (such as $Li_xTi_5O_{12}$). The material comprising the anode may be carried on foil (e.g., nickel and copper) backing or pressed into expanded metal screen and alloyed with various other metals.

Examples of suitable cathode materials include graphite, amorphous carbon, $Li_xCoO_2$, $Li_xNiO_2$, Co-doped $Li_xNiO_2$, $Li_xMn_2O_4$, $Li_xMnO_2$, $V_2O_5$, $V_6O_{13}$, $LiV_3O_8$, $Ba_2SmNiO_5$, $SmMnO_3$, $Sm_3Fe_5O_{12}$, $EuFeO_3$, $EuFe_5O_{12}$, $EuMnO_3$, $LaNiO_3$, $La_2CoO_4$ and $LaMnO_3$ (including the charged and discharged forms of these materials), and conducting polymers such as polypyrrole, polysulfides and polyvinylferrocene. In primary batteries, the cathode can be fluorinated carbon (e.g., $(CF)_n$), $SO_2Cl_2$, $Ag_2CrO_4$, sulfur, polysulfide, and an $O_2$ or $SO_2$ electrode.

Lithium batteries and supercapacitors usually contain a separator to prevent short-circuiting between the cathode and anode. The separator usually consists of a single-ply or multi-ply sheet of microporous polymer (typically polyolefin, e.g., polyethylene, polypropylene, or combinations thereof) having a predetermined length and width and having a thickness of less than 10 mils (0.025 cm). For example, see U.S. Pat. No. 3,351,495 (Larsen et al.), U.S. Pat. No. 4,539,256 (Shipman et al.), U.S. Pat. No. 4,731,304 (Lundquist et al.) and U.S. Pat. No. 5,565,281 (Yu et al.). The pore size in these microporous membranes, typically about 5 microns in diameter, is sufficiently large to allow transport of ions but is sufficiently small to prevent cathode/anode contact, either directly or from particle penetration or dendrites which can form on the electrodes.

The novel compounds of this invention can also be employed in non-electrolyte applications. For example, the salts of Formula I are useful as surfactants when the hydrocarbon groups of R and/or R' contain in the range of 8 to 18 carbon atoms or when the fluoroalkyl group of R' contains in the range of 4 to 12 carbon atoms. Examples of such usefull surfactant salt anions include $C_8F_{17}SO_2N^-SO2OCH(CH_3)_2$, $(C_{12}H_{25}OSO_2)_2N^-$ and $C_8F_{17}SO_2N^-SO_2OC_{12}H_{25}$; surfactant salt cations can be those commonly used in anionic surfactants, such as alkali metal, alkaline earth metal or ammonium. The salts and acids are also potentially useful as catalysts, antistats and as cationic photoinitiators; examples of such useful compounds are $C_6H_5OSO_2NHSO_2CF_3$, $(CH_3)4P^+$ $^-N(SO_2OC_6H_5)_2$ and $(C^6H_5)_3S^+$ $^-N(SO_2CF_3)(SO_2OC_6H_5)$.

The invention is illustrated further by, but is not intended to be limited to, the following examples.

EXAMPLES

Note: All electrolyte salt samples were stored and handled in a nitrogen- or argon-filled dry box (Vacuum Atmospheres Inc.) to prevent contamination by water.

Test Methods

Conductivity

Conductivity measurements for liquid electrolytes were generally made using a 1 molar (1M) electrolyte derived from carefully purified and dried components. The 1M electrolyte was made by dissolving 10 millimoles of electrolytic compound in 10 mL of a 50/50 (vol) mixture of propylene carbonate (PC)/1,2-dimethoxyethane (DME) or ethylene carbonate (EC)/dimethyl carbonate (DMC). 10 mL of the resulting electrolyte was placed in a glass container with a conductivity cell having K=1.0/cm (Model No. 3403, available from YSI Inc., Yellow Spring, Ohio), all kept in a dry box before use. During all times, water contamination in the electrolyte was kept below 30 ppm, as determined by Karl Fischer titration. Impedance response was then measured in milli-Siemens per square centimeter (mS/cm) using a PAR Model 273 potentiostat/galvanometer (available from EG&G Princeton Applied Research, Princeton, N.J.), equipped with a frequency response analyzer (Model 1260, available from Schlumberger, Billerica, Mass.). The impedance response for each cell was measured using an AC signal of 5–10 mv over a frequency response of 100,000 to 1 Hz, using Model 398 Electrochemical Software (available from EG&G Princeton Applied Research). The conductivity was then calculated from the impedance response.

Other concentrations, ranging from 0.2–2.0 M, were also evaluated to identify the concentration for maximum conductivity.

Sources, Preparations for Conductive Salts

Salt 1

17 g of catechol (1,2-dihydroxybenzene, available from Aldrich Chemical Co., Milwaukee, Wis.) was dissolved in 75 g of anhydrous acetonitrile. To this was added 42 g of imidobis(sulfuryl chloride) (prepared as described in "Inorganic Synthesis," Vol. VIII, 1966, p. 105) in 90 g of anhydrous acetonitrile. The resulting solution was cooled to 0° C., 85 g of anhydrous triethylamine was added dropwise, and the mixture was allowed to react by stirring for 1 hour at 0° C., followed by 1 hour at room temperature. The reaction mixture was filtered and the solvent was removed in vacu to give a brown-red oil. The resulting oil was neutralized with 660.6 g of aqueous 1M LiOH (99.995% pure, available from Aldrich Chem. Co.). The water was removed and the resulting solids were washed twice with 250 mL aliquots of diethyl ether. The ether was removed to give 32.6 g of a white solid, which was further purified by re-dissolving in tetrahydrofuran and passing the resulting solution through a short column of basic alumina. The recovered compound was identified as being

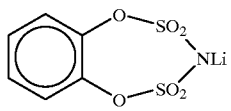

NMR analysis (CD$_3$CN): $^1$H, 7.27 ppm (m, 2H) 7.33 ppm (m, 2H), $^{13}$C, 118, 124, 128 ppm. Chloride ion content: 12 ppm as measured by argentometric titration using silver nitrate titrant. Elemental analysis: 28.33% C, 1.69% H, 5.28% N, 24.37% S, 2.59% Li, 37.74% O (theo. 28.02% C, 1.57% H, 5.45% N, 24.93% S, 2.70% Li and 37.33% O).

Salt 2

Salt 2, [(CH$_3$)$_2$CHOSO$_2$]$_2$NLi, was prepared using essentially the same procedure as described for Salt 1, except that isopropyl alcohol was reacted with imidobis(sulfuryl chloride) in the presence of excess triethylamine. NMR (D$_2$O): $^1$H, 1.33 ppm (d, 12H, J=6.5 Hz) 4.65 ppm (septet, 2H, J=6.5).

Salt 3

Salt 3, [(CH$_3$)$_2$NSO$_2$](CF$_3$SO$_2$)NLi, was prepared using essentially the same procedure as described for Salt 1, except that trifluoromethylsulfonamide was reacted with dimethylsulfamoyl chloride in the presence of excess triethylamine. NMR (CD$_3$CN): $^1$H, 2.62 ppm (s), $^{19}$F-77.9 ppm (s).

Salt 4

Salt 4,

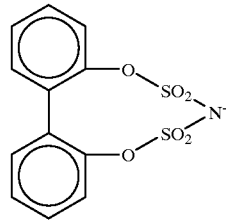

was prepared using essentially the same procedure as described for Salt 1, except that 8.6 g of 2,2'-dihydroxybiphenyl was reacted with 10.0 g of imidobis (sulfuryl chloride) in the presence of excess triethylamine, providing a 39% yield of the title product. $^1$HNMR (CD$_3$CN): δ=7.23 dd, 7.34 dt, 7.46 dt, 7.54 dd ppm. 13CNMR (CD$_3$CN): δ=123.7, 127.3, 130.5, 131.0, 131.9, 150.7 ppm MS negative ion laser desorption: M$^-$: m/z=326; [M$^-$-SO$_3$]: m/z=246; [M$^-$2SO$_3$]: m/z=166.

Salt 5

Salt 5, (C$_6$H$_5$)SO$_2$NLiSO$_2$N(CH$_3$)$_2$, was prepared using essentially the same procedure as described for Salt 1, except that benzenesulfonamide was reacted with dimethylsulfamoyl chloride in the presence of excess triethylamine.

The measured conductivities for Salts 1–5 are presented in Table 1.

TABLE 1

| Ex. | Compound Evaluated | Solvent Blend | Conductivity, MS/cm (molarity) |
|---|---|---|---|
| 1 | Salt 1 | EC / DMC | 7.2 (0.8M) |
| 2 | Salt 2 | EC / DMC | 2.0 (0.2M)* |
| 3 | Salt 3 | EC / DMC | 4.4 (0.6M) |
| 4 | Salt 4 | EC / DMC | 1.2 (1M) |
| 5 | Salt 5 | EC / DMC | 0.83 (0.2M)* |

*Salt solubility was low

The data in Table 1 show that all of the salts exhibited fair to good conductivity in the solvent blend. This is surprising, considering that the salts have little or no organofluorine in their structures. Salt 1, the fluorine-free catechol derivative, imparted especially high conductivity to the electrolyte.

We claim:

1. A homo- or copolymeric material comprising the reaction product of one or more compounds of the formula N$^-$(SO$_2$XR$_p$)$_m$(SO$_2$R')$_o$1/nM$^{n+}$ wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is each independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a heteroatom;

wherein R or R' contain a polymerizable group; and $M^{n+}$ is a cation having a valence of n.

2. The material of claim 1, wherein the polymerizable group is an olefinic unsaturated group, an epoxide group, an isocyanato group or a mixture thereof.

3. The material of claim 2, wherein the olefinic unsaturated group is a vinyl, allyl, acrylyl, methacrylyl group or a mixture thereof.

4. The material of claim 1, wherein R is a straight or branched aliphatic group, a cycloaliphatic group, phenyl or naphthyl, and wherein R is substituted by a polymerizable group.

5. The material of claim 4, wherein the polymerizable group is an olefinic unsaturated group, an epoxide group or an isocyanato group.

6. The material of claim 5, wherein the olefinic unsaturated group is a vinyl, allyl, acrylyl or methacrylyl group.

7. A compound of the formula

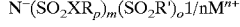
$N^-(SO_2XR_p)_m(SO_2R')_o 1/nM^{n+}$ wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is each independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a catenary heteroatom; and $M^{n+}$ is a cation having a valence of n; and wherein two R groups form an alkylene group, a 1,2-phenylene group, or a 1,1'-bis-phenylene group joined to two X atoms;

with the proviso that when m is 2, $M^{n+}$ is a metal or alkylammonium cation of the formula $R''_4N^+$, where R" is independently alkyl having 1 to 4 carbon atoms.

8. A compound of the formula

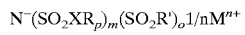
$N^-(SO_2XR_p)_m(SO_2R')_o 1/nM^{n+}$ wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is each independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a catenary heteroatom; and $M^{n+}$ is a cation having a valence of n; and wherein p is 2 and two R groups form an alkylene group forming a 3- to 6-membered ring with X;

with the proviso that when m is 2, $M^{n+}$ is a metal or alkylammonium cation of the formula $R''_4N^+$, where R" is independently alkyl having 1 to 4 carbon atoms.

9. A compound of the formula

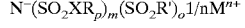
$N^-(SO_2XR_p)_m(SO_2R')_o 1/nM^{n+}$ wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is each independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a catenary heteroatom; and $M^{n+}$ is a cation having a valence of n; and wherein p is 1 or 2 and o is 1, and both R and R' form an alkylene group of 2 or 3 carbon atoms or a phenylene group joined at the 1,2-positions to form a ring;

with the proviso that when m is 2, $M^{n+}$ is a metal or alkylammonium cation of the formula $R''_4N^+$, where R" is independently alkyl having 1 to 4 carbon atoms.

10. A compound of the formula

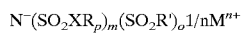

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is each independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a catenary heteroatom; and $M^{n+}$ is a cation having a valence of n;

wherein R is a member selected from the group consisting of $CH_3$—, $C_2H_5$—, $(CH_3)_2CH$—, $(CH_3)_3CCH_2$—, $C_8H_{17}$—, $C_6H_5$—, $C_{10}H_7$—, $H_3CC_6H_4$—, $O_2NC_6H_4$—, $FC_6H_4$—, $NCC_6H_4$—, $(CF_3)_2C_6H_3$—, $CH_2=CH_2$—, $CH_2=CHCH_2$—, $CH_2=C(CH_3)$—, $CH_2=CHC(O)OC_2H_4$—, $CH_2=C(CH_3)C(O)OC_2H_4$—, $CH_2=CH-C_6H_4$—, $HC\equiv CCH_2$—, $OCN(CH_2)_6NH$—, $OCN-C_6H_4$—, $HOC_2H_4$—, $HOCH_2CH(OH)CH_2$—, $H_2NC_2H_4$—, $(CH_3O)_3SiC_3H_6$—, $(CH_3O)_2(CH_3)SiC_3H_6$—,

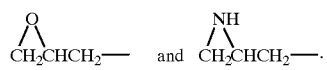

with the proviso that when m is 2, $M^{n+}$ is a metal or alkylammonium cation of the formula $R''_4N^+$, where R" is independently alkyl having 1 to 4 carbon atoms.

11. A compound of the formula

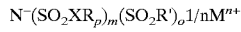

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is each independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkyl groups are uninterrupted or interrupted by a heteroatom; or an R group and an R' group when taken together may form a ring, which ring may be further interrupted by a catenary heteroatom; and $M^{n+}$ is a cation having a valence of n; and wherein two R groups form a member selected from the group consisting of —$CH_2CH_2$—, —$CH_2CH(CH_3)$—, —$CH_2=CH-C_6H_4$—,

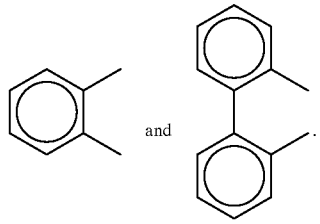

with the proviso that when m is 2, $M^{n+}$ is a metal or alkkylammonium cation of the formula $R''_4N^+$, where R" is independently alkyl having 1 to 4 carbon atoms.

12. A compound of the formula

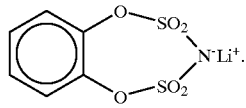

13. A compound of the formula $[(CH_3)_2CHOSO_2]_2N^-Li^+$.

14. A compound of the formula $[(CH_3)_2NSO_2](CF_3SO_2)N^-Li^+$.

15. A compound of the formula

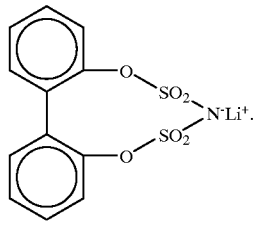

16. A compound of the formula $(C_6H_5)SO_2N^-Li^+SO_2N(CH_3)_2$.

17. A battery electrolyte comprising:

(a) a salt of the formula

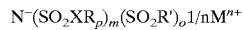

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkylene groups are uninterrupted or interrupted by a catenary heteroatom; or an R group and an R' group when taken together may form a ring, which ring may be further interrupted by a heteroatom; and $M^{n+}$ is a cation having a valence of n; and (b) a matrix material; and wherein two R groups form an alkylene group or 1,2-phenylene group joined to two X atoms.

18. A battery electrolyte comprising:
(a) a salt of the formula $$N^-(SO_2XR_p)_m(SO_2R')_o 1/nM^{n+}$$

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkylene groups are uninterrupted or interrupted by a catenary heteroatom; or an R group and an R' group when taken together may form a ring, which ring may be further interrupted by a heteroatom; and $M^{n+}$ is a cation having a valence of n; and (b) a matrix material, and wherein R is a member selected from the group consisting of $CH_3$—, $C_2H_5$—, $(CH_3)_2CH$, $(CH_3)_3CCH_2$—, $C_8H_{17}$—, $C_6H_5$—, $C_{10}H_7$—, $H_3CC_6H_4$—, $O_2NC_6H_4$—, $FC_6H_4$—, $NCC_6H_4$—, $(CF_3)_2C_6H_3$—, $CH_2$=$CH_2$—, $CH_2$=CH—$CH_2$—, $CH_2$=CHC(O)—, $CH_2$=C($CH_3$)C(O)—, $CH_2$=CHC(O)O$C_2H_4$—, $CH_2$=C($CH_3$)C(O)O$C_2H_4$—, —$CH_2CH_2$—, —$CH_2$CH($CH_3$)—, —$CH_2$=CH—$C_6H_4$—, HC≡C$CH_2$—, OCN($CH_2$)$_6$NHC(O)—, OCN—$C_6H_4$—, HO$C_2H_4$—, HOCH$_2$CH(OH)CH$_2$—, $H_2NC_2H_4$—, $(CH_3O)_3SiC_3H_6$—, $(CH_3O)_2(CH_3)SiC_3H_6$—,

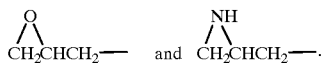
and

19. A battery electrolyte comprising:
(a) a salt of the formula $$N^-(SO_2XR_p)_m(SO_2R')_o 1/nM^{n+}$$

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkylene groups are uninterrupted or interrupted by a catenary heteroatom; or an R group and an R' group when taken together may form a ring, which ring may be further interrupted by a heteroatom; and $M^{n+}$ is a cation having a valence of n; and (b) a matrix material wherein R is a straight or branched aliphatic group, a cycloaliphatic group, phenyl or naphthyl, and wherein R is substituted by a reactive group, wherein the reactive group is polymerizable.

20. By A battery electrolyte comprising:
(a) a salt of the formula $$N^-(SO_2XR_p)_m(SO_2R')_o 1/nM^{n+}$$

wherein:

m is 1 or 2 and m+o is 2;

X is independently O or N;

p is 1 when X is O, and p is 2 when X is N;

R is each independently a monovalent hydrocarbon group; two R groups when taken together form a divalent hydrocarbon group joined to two X atoms, in which the hydrocarbon groups are uninterrupted or interrupted by a heteroatom; or two R groups when taken together may form a three- to six-membered ring with a nitrogen atom, which ring may be further interrupted by a heteroatom;

R' is independently a hydrocarbon group or a straight or branched acyclic fluoroalkyl group having from 1 to 12 carbon atoms, a cyclic fluoroalkyl group having from 3 to 12 carbon atoms, or a fluorocycloalkyl-fluoroalkyl group where the fluoroalkyl group has from 1 to 4 carbon atoms, in which the fluoroalkyl and fluorocycloalkylene groups are uninterrupted or interrupted by a catenary heteroatom; or an R group and an R' group when taken together may form a ring, which ring may be further interrupted by a heteroatom; and $M^{n+}$ is a cation having a valence of n; and (b) a matrix material, and wherein two R groups form a member selected from the group consisting of

—$CH_2CH_2$—, —$CH_2CH(CH_3)$—, —$CH_2$=$CH$—$C_6H_4$—,

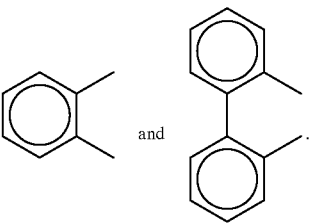

and

* * * * *

UNITED STATES PATENT AND TRADEMARK OFFICE
CERTIFICATE OF CORRECTION

PATENT NO. : 6,350,545 B2
DATED : February 26, 2002
INVENTOR(S) : Fanta, Alan D.

It is certified that error appears in the above-identified patent and that said Letters Patent is hereby corrected as shown below:

Column 2,
Line 33, "2and" should read -- 2 and --;

Column 3,
Line 2, "2and" should read -- 2 and --;
Line 50, "jonically" should read -- ionically --;

Column 10,
Line 53, "usefull" should read -- useful --;
Line 53, "SO2OCH" should read -- $SO_2OCH$ --;
Line 60, "$(CH_3)4P^+$" should read -- $(CH_3)_4P^+$ --;
Line 61, "$(C^6H_5)_3S^+$" should read -- $(C_6H_5)_3S^+$ --;

Column 11,
Lines 39 and 40, "in vacu" should read -- *in vacu* --;
Line 66, "6.5 Hz" should read -- 6.5Hz --;

Column 15,
Line 33, "n;" should read -- n; and --; and
Line 51, "$^{where\ R}$ is" should read -- where R" is --

Signed and Sealed this

Twenty-second Day of October, 2002

Attest:

JAMES E. ROGAN
Attesting Officer   Director of the United States Patent and Trademark Office